US006379705B1

(12) United States Patent
Mendes et al.

(10) Patent No.: US 6,379,705 B1
(45) Date of Patent: Apr. 30, 2002

(54) STABLE MULTI-UNITARY PHARMACEUTICAL PREPARATIONS CONTAINING SUBSTITUTED BENZIMIDAZOLES

(75) Inventors: Carla Patricia Goncalves Mendes; Maria Julia Caeiro Ramalho De Oliveira, both of Sacavem (PT)

(73) Assignee: Laboratorio Mendifar-Produtos Farmaceuticos, S.A.

( * ) Notice: Subject to any disclaimer, the term of this patent is extended or adjusted under 35 U.S.C. 154(b) by 0 days.

(21) Appl. No.: 09/580,551

(22) Filed: May 30, 2000

(30) Foreign Application Priority Data

Dec. 16, 1999 (EP) .............................. 99670010

(51) Int. Cl.$^7$ .............................. A61K 9/16; A61K 9/50
(52) U.S. Cl. .............................................. 424/490
(58) Field of Search ........................................ 424/490

(56) References Cited

FOREIGN PATENT DOCUMENTS

EP            773025      *   5/1997

* cited by examiner

Primary Examiner—Alton Pryor
(74) Attorney, Agent, or Firm—Sughrue Mion, PLLC (57) ABSTRACT

The present invention relates to oral multi-unitary pharmaceutical preparations containing substituted benzimidazoles being inhibitors of $H^+$, $K^+$-ATPase (i.e. omeprazole, lansoprazole, pantoprazole, leminoprazole and pariprazole) or their pharmaceutically acceptable salts. Such pharmaceutical preparations are stable pellet preparations containing substituted benzimidazole(s) or their salts and they comprise a quantity of active ingredient of between 1 and 50 mg, an inert core of spherical symmetry with a diameter of 600–1000 $\mu$m, constituted by inert excipients, coated with an active layer containing at least one substituted benzimidazole in the micronized form and various pharmaceutically acceptable inert excipients, mixed in suitable proportions in order to allow the disaggregation of the formulations and dissolution of the active ingredient(s) in an appropriate manner, coated in turn with an insulating layer of a strictly polymeric nature, soluble in water, free from alkaline and/or alkaline-earthy metallic salts, of a minimum thickness of 15 $\mu$m, this layer being coated lastly with a gastroresistant or enteric layer of a minimum thickness of 30 $\mu$m. This invention also refers to the process for the preparation of said pharmaceutical preparations.

13 Claims, 4 Drawing Sheets

Graphic representation of the results obtained for the stability tests carried out at 40°C/75% relative humidity with a batch of omeprazole pellets.

Figure 1

Graphic representation of the results obtained for the stability tests carried out in real time with a batch of omeprazole pellets.

Figure 2

Graphic representation of the results obtained for the stability tests carried out at 40°C/75% relative humidity with a batch of lansoprazole pellets.

Figure 3

Graphic representation of the results obtained for the stability tests carried out in real time with a batch of lansoprazole pellets.

Figure 4

STABLE MULTI-UNITARY PHARMACEUTICAL PREPARATIONS CONTAINING SUBSTITUTED BENZIMIDAZOLES

FIELD OF THE INVENTION

The present invention relates to new oral multi-unitary pharmaceutical preparations containing substituted benzimidazoles being inhibitors of $H^+$, $K^+$-ATPase (i.e. omeprazole, lansoprazole, pantoprazole, leminoprazole and pariprazole) or their pharmaceutically acceptable salts. The preparations comprise a spherical inert core, constituted by starch and sugar, coated with a layer containing at least one substituted benzimidazole in the micronized form, which is mixed with pharmaceutically acceptable inert excipients, whose proportions are suitable for allowing the disaggregation of the dosage forms and the intended dissolution of the active ingredient(s), this layer in turn being coated with an insulating layer of an exclusively polymeric nature and of suitable thickness, applying lastly an external, gastroresistant or enteric layer of suitable thickness, in order to guarantee the integrity of the product until it reaches the proximal part of the small intestine, where the formulation will be disaggregated to facilitate the absorption of the substituted benzimidazolic compounds. The pellets produced according to the invention are placed in hard gelatine capsules and administered to patients in this form. The invention does not require the stabilization of the benzimidazolic compounds using any of the strategies or processes which already belong to the state of the art. Besides, the pharmaceutical products produced in this way are free from organic solvents and/or the impurities generally associated to them, because the application of the different layers exclusively requires aqueous solvents. This aspect constitutes a technological advantage, since the manufacturing process is incomparably safer, because there is no toxicity risk to operators or explosion risks and moreover it is more ecological, because there is no possibility of environmental contamination caused by organic solvents leaking into the atmosphere. Finally, it is much safer for the patient, because there is no need to consider solvents and/or residual impurities associated to them, which is a considerable advantage in terms of public health. For the manufacture of the products, only equipment is required—a fluid bed equipment with an inner partition device (wurster). The products obtained by extrusion/spheronization, by rotogranulation or by "powder coating" are completely outside the scope of the present invention.

The products obtained are stable for a period of time compatible with pharmaceutical requirements, and they present gastroresistance and dissolution characteristics generally adapted to the period of validity established for pharmaceutical products (i.e. 3 years).

BACKGROUND OF THE INVENTION

Benzimidazolic compounds such as omeprazole (5-methoxy-2(((4-methoxy-3,5-dimethyl-2-pyridinyl)-methyl-sulfinyl)1H-benzimidazole (EP-B1-0005129), lansoprazole (2-((3-methyl-4-(2,2,2-trifluoroetoxy)-2-piridyl) methyl(sulfinyl 1H-benzimidazole) (U.S. Pat. No. 4,628, 098), pantoprazole (U.S. Pat. No. 4,758,579)), leminoprazole and pariprazole are anti-ulcerous substances known for decreasing gastric acid secretion (Olbe L., et al., Gastroenterol., 83:193–198 (1982); Saton H. et al., Jpn. J. Pharmacol. 40 (suppl.), 226 (1986); Saton H, et al., J.Pharmacol. Exp. Ther, 248 (2), 806–815 (1989), Nagaya, H et al., J.Pharmacol. Exp. Ther., 248 (2), 799–805 (1989)) and they are used in the therapeutics of diseases related to gastric acidity in mammals and especially in humans, including gastric and duodenal ulcers, reflux oesophagitis, gastritis, duodenitis and Zollinger-Ellison syndrome.

It is also known that these substituted benzimidazoles possess a very low level of solubility in water, they solubilize easily in alkaline solutions (i.e. the $t_{1/2}$ of degradation of omeprazole in aqueous solutions of pH>11 is 600 days), they degrade quickly in acidic and neutral media (i.e. the $t_{1/2}$ of degradation of omeprazole in aqueous solutions of pH<4 is 10 minutes) (Pilbrand and Cederberg, Scand. J. Gastroenterol, 20 (Suppl. 108), p. 113–120 (1985)) and they are stabilized in the presence of alkaline reacting compounds. The maximum stability of omeprazole solutions is reached at pH 11; for pHs lower than 7.8, degradation occurs very quickly (Drug.Dev.Ind.Pharm., 21(8), 965 (1995). Lansoprazole is relatively stable when exposed to the light. This compound degrades in aqueous solution, its degradation speed increasing as the pH decreases. For this reason, whenever the oral route is used it is indispensable to coat the formulations with a gastroresistant layer, in order to avoid contact between the active ingredient and gastric content with acidic characteristics. On the other hand, it is necessary that the formulations dissolved quickly in the intestine, where the benzimidazolic compounds should be absorbed, i.e. when the pH becomes higher than 6.8. Several pharmaceutical preparations containing substituted benzimidazole inhibitors of $H^+,K^+$-ATPase are already patented.

The first assays performed with classic enteric pellets containing omeprazole showed that they did not present suitable stability during a long enough period of time to be used in a satisfactory pharmaceutical dosage form, because fast degradation of the active ingredient was observed when subjected to normal conditions of storage (T=25±1° C. and HR=40–75%), with the appearance of noxious degradation products (Brandstrom A., et al., Acta Chemica Scandinavia, 43, 536–548 (1989)).

DE-A1-3046 559 describes a way to coat a pharmaceutical dosage form with an insoluble layer containing microcrystalline cellulose and with a second enteric layer. This preparation did not allow the desirable release of omeprazole in the small intestine.

U.S. Pat. No. 2,540,979 describes a preparation coated with an enteric layer combined with a first coating of a water-insoluble wax. This preparation was shown to be inadequate for omeprazole because the direct contact of the cellulose acetophtalate (CAP) with the omeprazole caused its degradation.

DE-A1-1 204 363 describes a pharmaceutical dosage form which has three layers but cannot be used for omeprazole because it does not allow the fast release of omeprazole in the small intestine, as is desirable. DE-A1-1 204 363 concerns a coating that allows the delivery of the active ingredient in the ileum, which is not desirable in the case of omeprazole.

DE-A1-1 617 615 describes a dosage form which likewise cannot be applied to omeprazole because it is dissolved very slowly in the intestinal juice.

GB 2 189 698 A and U.S. Pat. No. 4,786,505 propose the mixture of a mass of cellulose derivatives and disaggregants, with an appropriate amount of omeprazole and alkaline salts, in order to obtain, by extrusion, a core which is spheronized and coated with gastroresistant agents dissolved in alcoholic solutions also containing considerable percentages of acetone. However, the pellets obtained are extremely irregular in shape and dimensions, which hinders the process of filling the gelatine capsules, and this can have repercussions on a relative dispersion of the average weight of the capsules and of the respective dosage. Besides, the use of organic solvents in any of the phases of preparation of the pharmaceutical dosage forms means that the quantity thereof in the final product will have to be determined, as well as the quantity of the impurities that may be associated to them and may be potentially dangerous for the health, which makes them highly inadvisable.

U.S. Pat. No. 5,232,706 describes omeprazole dosage forms coated with one or more layers containing water-soluble alkaline excipients mixed with a second alkaline compound.

U.S. Pat. No. 5,385,739 and FR-A-2 692 146 describe pharmaceutical gastroprotected dosage forms containing omeprazole wherein the active substance is diluted with mannitol and applied to an inert core. The dosage form is prepared in a conventional coating pan, which is a slow process and requires the use of organic solvents which are noxious to the operator and dangerous to handle. Besides, with the pellets obtained, with a wrinkled surface, it is difficult to fill capsules of uniform weight. Finally, the pellets marketed by the applicant of these patents did not observe the gastroresistance and dissolution criteria required for their use during the period of validity established for pharmaceutical dosage forms.

U.S. Pat. No. 5,399,700 concerns the stabilization of benzimidazolic derivative compounds as cyclodextrin inclusion complexes.

U.S. Pat. No. 5,690,960 concerns dosage forms containing magnesium omeprazole salts with more than 70% crystallization.

U.S. Pat. No. 5,708,017 concerns an oral formulation in the form of a paste in an oily vehicle, containing a proton pump inhibitor, intended for the treatment of gastric ulcers in humans and animals.

U.S. Pat. No. 5,714,504 relates to pharmaceutical formulations for oral administration containing alkaline salts of the (−) enantiomer of omeprazole.

WO 96/01623 relates to omeprazole tablets obtained from gastroresistant multi-unitary dosage forms, which are used to prepare tablets in the presence of appropriate excipients.

WO 97/12581 relates to oral formulations of omeprazole obtained by compression of pellets containing benzimidazoles, thereby obtaining micro-tablets which are subsequently coated and placed in hard gelatine capsules.

WO 98/53803 relates to the specific use of a quality of HPMC in the manufacture of pharmaceutical dosage forms containing omeprazole.

WO 98/19668 relates to an omeprazole formulation with pulsatile kinetics which simulates a bolus for a once-a-day dosage form.

WO 98/50019 relates to oral dosage forms containing omeprazole or lansoprazole, inside hard gelatine capsules which are subsequently coated with gastroresistant or enteric polymers.

U.S. Pat. No. 4,689,333 describes pharmaceutical compositions for the prevention or treatment of ulcers containing an effective amount of lansoprazole or a pharmaceutically acceptable salt thereof.

U.S. Pat. No. 5,026,560 relates to spherical pellets consisting of a core coated with a binding agent which is coated with a mixture of powders containing lansoprazole, HPMC of low viscosity and magnesium or calcium carbonates as alkaline agents. The manufacturing process used was "powder coating", which is difficult and laborious and therefore makes the product very expensive.

U.S. Pat. No. 5,045,321 relates to dosage forms for the production of pellets or coated tablets which comprise a uniform mixture of lansoprazole with at least one alkaline inorganic salt. There is no reference to protective and/or enteric coatings in the claims of the patent.

U.S. Pat. No. 5,093,132 claims a stable oral dosage form containing lansoprazole or a pharmaceutically acceptable salt thereof mixed uniformly with an alkaline inorganic salt as a stabilizing agent. Only a simple reference is made to the use of an enteric coating.

EP 0 589 981 relates to oral dosage forms of pantoprazole as tablets or pellets which use alkaline and/or alkaline-earthy metallic salts for stabilization of the active ingredient and which use organic solvents (i.e. isopropanol) in the technological process for the production of the pharmaceutical formulations.

WO 97/12580 describes oral dosage forms of substituted benzimidazoles, preferably pantoprazole, obtained by compression of pellets containing benzimidazole, thereby producing micro-tablets that are subsequently coated and placed inside hard gelatine capsules.

The present invention concerns stable multi-unitary dosage forms of gastroresistant pellets for oral administration, free from residues of organic solvents and the impurities associated to them, containing a substituted benzimidazole or a pharmacologically acceptable salt thereof, or associations of substituted benzimidazoles or of their pharmaceutically acceptable salts. The formulations do not comprise any of the methods of stabilization of benzimidazoles already known from the state of the art and they are the first ones whose manufacturing process involves the use of a fluid bed equipment with an inner partition device (wurster), and not extrusion/spheronization techniques, rotogranulation, "powder coating" or coating in conventional coating pans. Thus, the present invention describes pellet formulations composed of an inert core coated with a layer which contains the active ingredient(s), coated in turn with an intermediate layer of a minimum thickness of 15 $\mu$m and with a final external gastroresistant or enteric layer of a minimum thickness of 30 $\mu$m. The thickness of the intermediate layer is decisive to the stability of the final product and it prevents the incorporation of alkaline and/or alkaline-earthy metallic salts into the mixture containing the benzimidazolic compounds, as well as into the insulating layer. The pellets obtained have spherical symmetry and their surface is perfectly flat when observed by scanning electronic microscopy (S.E.M.), contrary to the other formulations on the market that are obtained by other methods. In addition, the fact that the products are manufactured without the use of organic solvents makes them safer for patients and for operators who manufacture and handle them. The manufacturing process does not cause environmental pollution problems, which are becoming increasingly essential to avoid, and this is another of the aspects that differentiate these formulations from those belonging to the state of the art. Moreover, the process for manufacturing these new formulations has technical as well as economic advantages. In fact, all the stages of the manufacturing process use the same equipment, which represents less contact for the operator with the product, contrary to what happens with the other described processes which require the transfer of the pellets from the extruder/spheronizer to the coating pans or fluid bed equipments in order to be coated. Neither does it involve various equipments of restricted use and a high cost, which would have to be reflected in the final price of the product to consumers. These facts, together with the high market prices of benzimidazolic compounds, lead to an exaggerated increase in the price of the final product, which will necessarily be borne by patients who need the medication. The present invention seeks to reduce the production costs of these products in order that they can be used on a large scale all over the world.

SUMMARY OF THE INVENTION

The present invention describes multi-unitary pharmaceutical dosage forms containing a substituted benzimidazole (omeprazole, lansoprazole or pantoprazole, leminoprazole or pariprazole) or a salt thereof, or associations of benzimidazoles or their salts, constituted by a succession of layers arranged around an inert, spherical core, prepared in a fluid bed equipment with an inner partition device (wurster). The component elements of the dosage form are:

(1) inert core, (2) active layer, (3) insulating layer and (4) gastroresistant or enteric coating layer.

The inert cores of dimensions of 600–710 $\mu$m, 710–850 $\mu$m or 850–1000 $\mu$m, constituted by pharmaceutically acceptable inert excipients are coated with a layer containing at least one benzimidazole or its salts, mixed with pharmaceutically acceptable inert excipients, so that this layer is quickly disaggregable. This layer is then coated with an insulating layer of a strictly polymeric nature, of a minimum thickness of 15 $\mu$m, and finally this layer is coated with an enteric coating layer of a minimum thickness of 30 $\mu$m. The pellets have spherical symmetry and a flat surface, are free from residues of organic solvents and the impurities associated to them and they have a moisture level that guarantees good stability under normal storage conditions. The pellets are placed in hard gelatine capsules and it is in this form that they are administered to patients. The formulations with this composition are characterized in that they do not dissolve in an acid medium, but dissolve quickly at an alkaline pH and present good stability in terms of dosage and in gastroresistance and dissolution assays, when stored for at least 3 years.

BRIEF DESCRIPTION OF THE FIGURES

In order to test the stability of the finished products in their packaged form, industrial batches of omeprazole and lanzoprazole pellets were prepared (i.e. 400,000 capsules/batch), which were placed inside hard gelatine capsules, which were in turn stored in polyamide/aluminium/PVC blisters sealed with aluminium foil of 25 $\mu$m. The blisters were incubated in climatic chambers at 25° C. and 60% relative humidity (atmospheric conditions) and 40° C. and 75% relative humidity (accelerated assays). The following parameters were periodically determined: dosage, gastroresistance, dissolution and level of impurities.

FIG. 1 shows a graph of the dosage, gastroresistance and dissolution results obtained for omeprazole pellets stored inside blisters and kept at 40° C. and 75% relative humidity (accelerated assays) for 9 months. As can be seen, the omeprazole content is never lower than 95%, which is the minimum amount generally admissible for the amount of active ingredient in pharmaceutical forms during the period of validity. As can also be seen in FIG. 1, the gastroresistance value obtained for the period during which the assay was carried out was never lower than 85%, which is the minimum percentage generally accepted for gastroresistant formulations during the period of validity. Also as regards the dissolution assay, the value determined for this parameter for the period during which the assay was carried out was never lower than 75%, which is the minimum value generally accepted for this type of formulation during the period of validity. The values obtained for each of the parameters studied are presented in detail in Table V.

FIG. 3 shows a graph of the dosage, gastroresistance and dissolution results obtained for lansoprazole pellets stored inside blisters and kept at 40° C. and 75% relative humidity (accelerated assays) for 6 months. As can be seen, the lansoprazole content is never lower than 95%, which is the minimum amount generally admissible for the amount of active ingredient in pharmaceutical forms during the period of validity. As can also be seen in FIG. 3, the gastroresistance value obtained for the period during which the assay was carried out was never lower than 85%, which is the minimum percentage generally accepted for gastroresistant formulations during the period of validity. Also as regards the dissolution assay, the value determined for this parameter for the period during which the assay was carried out was never lower than 75%, which is the minimum value generally accepted for this type of formulation during the period of validity. The values obtained for each of the parameters studied are presented in detail in Table VII.

DETAILED DESCRIPTION OF THE INVENTION

Figure 1:
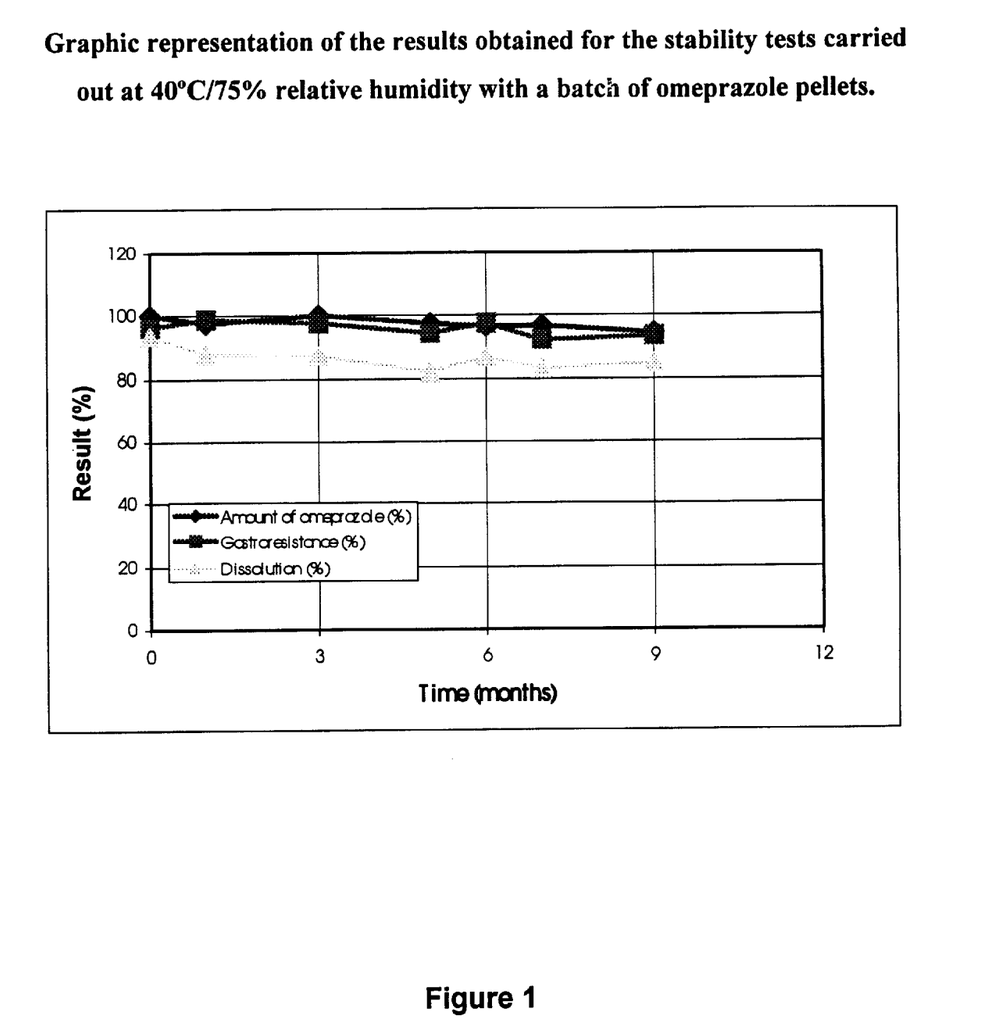
Figure 2:
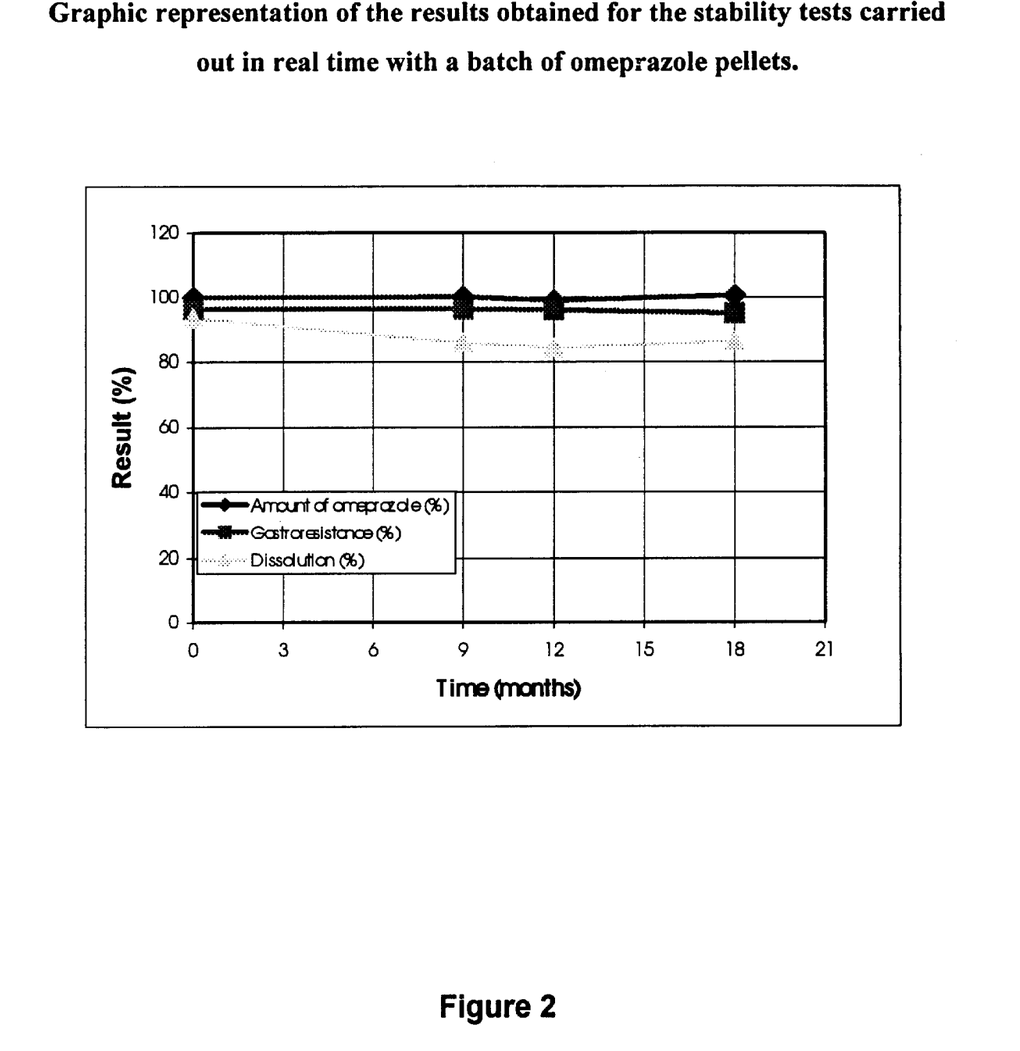
FIG. 2 shows a graph of the dosage, gastroresistance and dissolution results obtained for omeprazole pellets stored inside blisters and kept at 25° C. and 60% relative humidity (assays in real time or under atmospheric conditions) for 18 months. As can be seen, the omeprazole content is never lower than 95%, which is the minimum amount generally admissible for the dosage of active ingredient in pharmaceutical forms during the period of validity. As can also be seen in FIG. 2, the gastroresistance value obtained for the period during which the assay was carried out was never lower than 85%, which is the minimum percentage generally accepted for gastroresistant formulations during the period of validity. Also as regards the dissolution assay, the value determined for this parameter for the period during which the assay was carried out was never lower than 75%, which is the minimum value generally accepted for this type of formulation during the period of validity. The values obtained for each of the parameters studied are presented in detail in Table VI.
Figure 3:
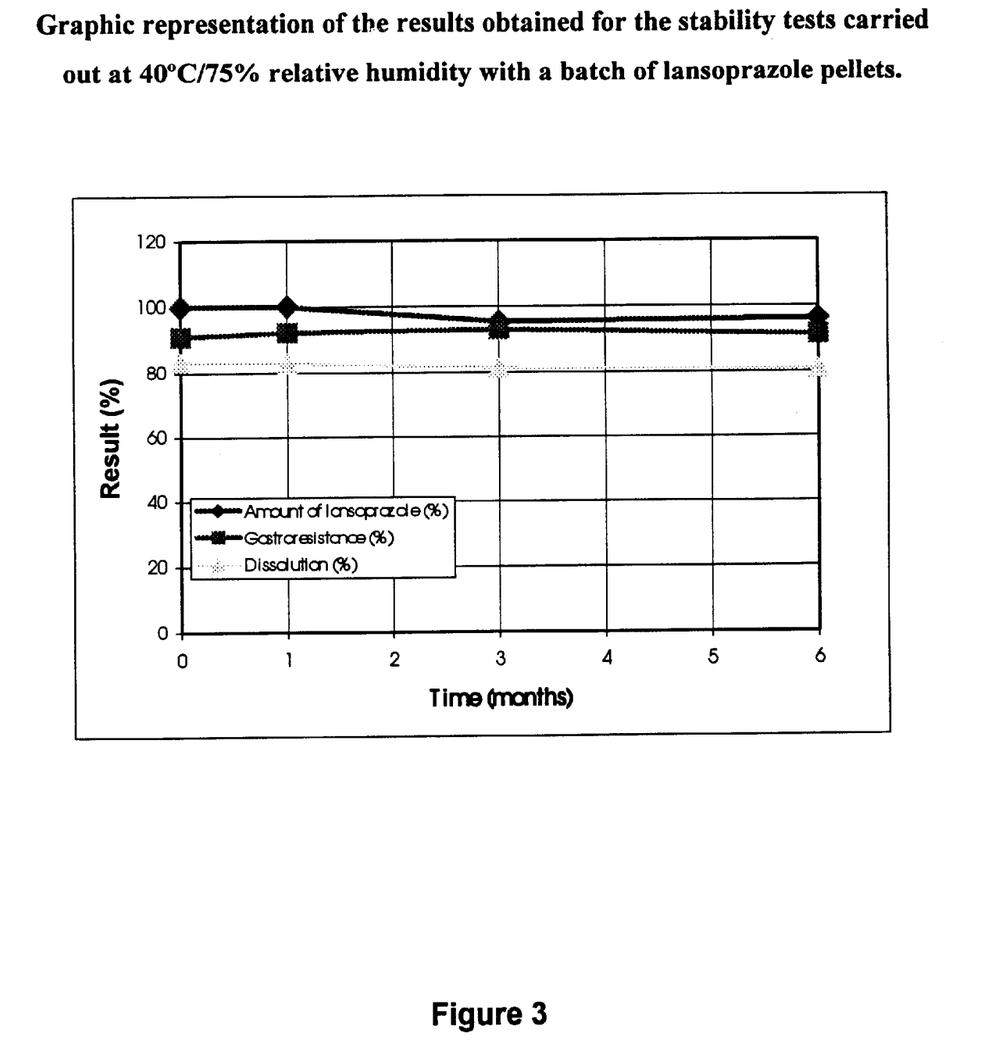
Figure 4:
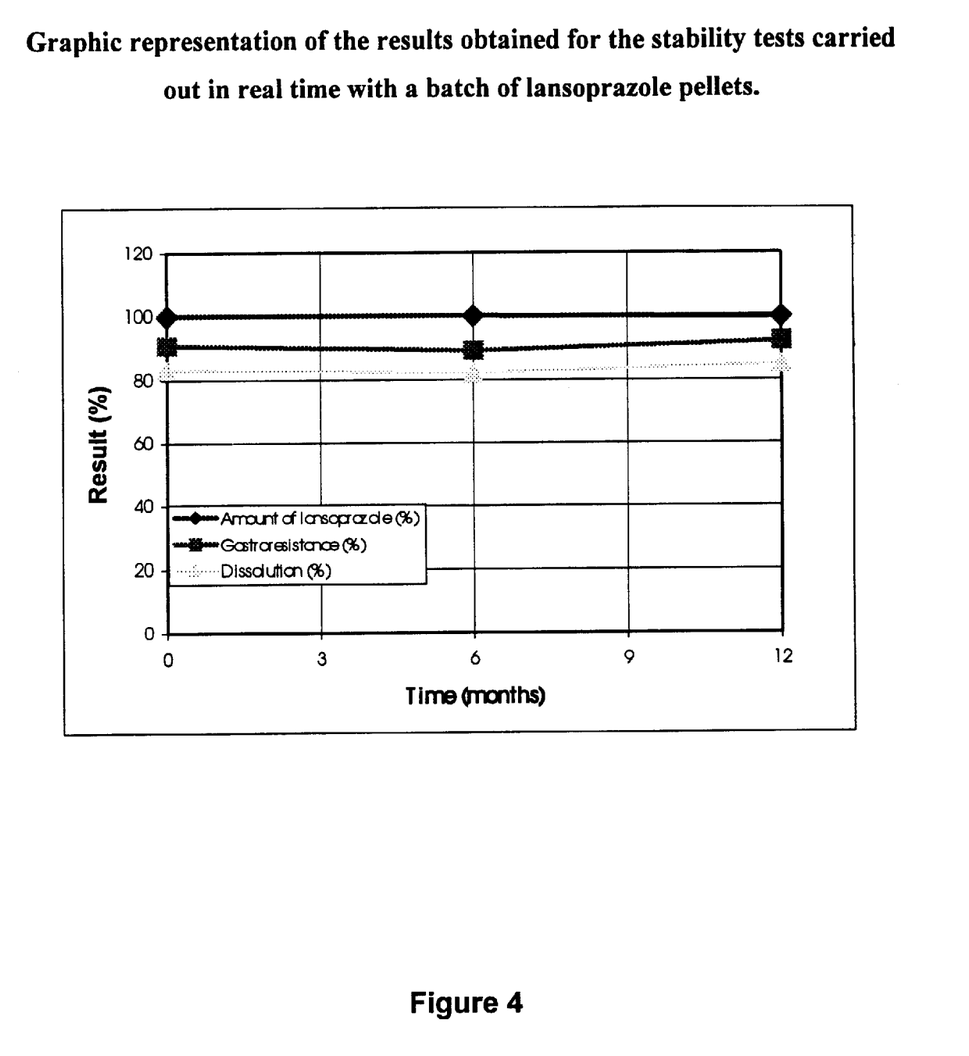
FIG. 4 shows a graph of the dosage, gastroresistance and dissolution results obtained for lansoprazole pellets stored inside blisters and kept at 25° C. and 60% relative humidity (assays in real time or under atmospheric conditions) for 12 months. As can be seen, the lansoprazole content is never lower than 95%, which is the minimum amount generally admissible for the dosage of active ingredient in pharmaceutical forms during the period of validity. As can also be seen in FIG. 4, the gastroresistance value obtained for the period during which the assay was carried out was never lower than 85%, which is the minimum percentage generally accepted for gastroresistant formulations during the period of validity. Also as regards the dissolution assay, the value determined for this parameter for the period during which the assay was carried out was never lower than 75%, which is the minimum value generally accepted for this type of formulation during the period of validity. The values obtained for each of the parameters studied are presented in detail in Table VIII.

The present invention describes formulations that comprise an inert core of spherical symmetry constituted by pharmaceutically acceptable inert excipients, coated with a succession of layers, in order to produce final multi-unitary gastroresistant formulations (pellets) that are placed in hard gelatine capsules. Another advantage of these new formulations is that all the stages of their production always take place in the same equipment and do not require the use of organic solvents. For this reason, these pharmaceutical preparations are safer for operators during their manufacture and for the patients to whom they are administered.

The elements to consider in the formulations are the following:

I. Inert cores.

II. Active layer.

III. Insulating layer.

IV. Gastroresistant or enteric layer.

I. Inert Cores

The inert cores have dimensions of 600–710 $\mu$m, 710–850 $\mu$m, or 850–1000 $\mu$m, according to the benzimidazole potency that is intended in the final product. The inert cores are constituted by starch (10–30%) and sucrose (60–90%), but can also contain glucose, lactose, mannitol or any other pharmaceutically acceptable inert excipients. With solid consistency and spherical symmetry, the inert cores are obtained from sucrose particles by coating them with successive layers of sucrose and cornstarch. The final product must contain less than 4% humidity. The particles must be selected in a relatively narrow range of granulometry, so that the pellets obtained at the end are of a uniform dimension. For the benzimidazole dosages generally used in therapeutics (i.e. generally 20–40 mg/capsule), the inert cores should not exceed 850 $\mu$m, so that gelatine capsules of a relatively small dimension can be used, which helps the patient to adhere to the therapy being followed. The inert cores can be obtained commercially and do not constitute the aim of the present invention.

II. Active Layer

The active layer is applied to the inert core and it contains at least one micronized benzimidazole (i.e. omeprazole, lansoprazole, pantoprazole, leminoprazole or pariprazole) or its pharmacologically acceptable salts and excipients that are also pharmaceutically acceptable, for example surfactant agents, such as sodium trilaurylphosphate, sodium dodecyl sulfate, sodium tridecylethoxylate, sodium myristylsulfate, or, preferentially, fatty acids of sorbitan esters, such as glycerol polyethyleneglycol oxystearate (Cremophor® of BASF Corporation), which increase the wettability of the benzimidazolic compounds; binding agents of a polymeric nature, such as hydroxymethylpropylcellulose (Pharmacoat® of Shinetsu; Methocel® of Colorcon), hydroxypropylcellulose (Klucel® of Hercules), hydroxymethylcellulose, hydroxyethylcellulose (Natrosol® of Hercules or Cellosize® of Union Carbide Corporation), methylcellulose (Methocel® A of Colorcon), ethylcellulose (Aquacoat® of FMC or Surealease® of Colorcon), polyvinylpyrrolidone (Povidone® of GAF Corp., Kollidon® of BASF), polyethylene glycols, etc. The mixture that constitutes the layer also contains sodium tetraborate to improve the solubility and stability of the benzimidazoles. In order for the dosage form to dissolve quickly disintegrating agents are added, such as sodium starch glycolate (Explotab® of Mendell, Primogel® of Generichem), pregelatinized starch (Starch 1500), microcrystalline cellulose (Avicel of FMC), sodic or calcic carboxymethylcellulose or sodium alginate. Lubricant agents such as magnesium or calcium stearate, or preferentially talc, should be added, in order to decrease the friction between the particles. The suspension containing the mixture of the ingredients is prepared exclusively in water. For the suitable preparation and application of the suspension, the inclusion of anti-foaming agents such as simethicone is advisable, preferentially in a form which is easily dispersible in water (in the form of an emulsion containing not less than 85% polydimethylsiloxane).

When used in the appropriate proportions, the substances previously mentioned are mixed with the active ingredient in an aqueous solution, are atomized on the inert cores under suitable conditions, producing a uniform layer of a thickness of between 150 and 250 $\mu$m.

III. Insulating Layer

An insulating layer is applied to the active layer in order to separate the layer containing the benzimidazole(s) from the enteric coating layer. In fact, gastroresistant polymers generally have free carboxyl groups with acidic characteristics, meaning that if they were to come into direct contact with the benzimidazoles they would cause the degradation thereof. For this reason, an insulating layer should be inserted between the active layer and the enteric coating layer.

The insulating layer contains binding agents of a polymeric nature which, by virtue of the evaporation of the solvent (i.e. demineralized water), form a protective layer. The binding agents of the insulating layer should be chosen among hydroxypropylmethylcellulose (Pharmacoat® of Shinetsu; Methocel® of Colorcon), hydroxypropylcellulose (Klucel® of Hercules), hydroxymethylcellulose, hydroxyethylcellulose (Natrosol® of Hercules or Cellosize® of Union Carbide Corporation), methylcellulose (Methocel® A of Colorcon), ethylcellulose (Aquacoat® of FMC or Surealease® of Colorcon), polyvinylpyrrolidone (Povidone® of GAF Corp., Kollidon® of BASF), polyethylene glycols, etc. The dispersion obtained, of suitable viscosity, is applied to the granules already containing the active ingredient layer. The thickness of this layer will not be less than 15 $\mu$m. Experimentally, it was ascertained that when this layer is not thick enough to suitably protect the layer containing the active ingredient(s) from contact with the enteric coating layer, the product is degraded quickly and darkens, and the gastroresistance of the final product quickly reaches values lower than 85%. Thus, the nature and thickness of this intermediate layer was found to be decisive to the stability of the final product. The composition of this layer, of a strictly polymeric nature, provided that it is of appropriate thickness, prevents the incorporation of alkaline and alkaline-earthy metallic salts into the intermediate layer in order to ensure the stability of the product.

V. Gastroresistant (or Enteric) Coating Layer

In the pharmaceutical dosage form, the enteric coating layer is applied to the insulating layer and it contains anionic copolymers of methacrylic acid and ethyl acrylate (Eudragit® L30D, Eudragit® L30D-55, Eudragit® L100-55 of Rohm & Hass), or latex of cellulose acetophtalate (CAP), such as Aquateric® of FMC, pharmaceutically acceptable plasticizers, such as triethylcitrate (Citroflex®-2), tributylcitrate (Citroflex®-4), acetyltributylcitrate (Citroflex®-A4), dibutyl sebacate (DBS), diethylphtalate (DEP), acetylated monoglyceride (Myvacet® 9-40), polyethylene glycols or 1,2-propylene glycol, and possibly a lubricant such as talc or colloidal silicon dioxide (Aerosil® 200 of Degussa) and an anti-foaming agent in the nature of silicone. The amounts of polymer and plasticizer have to be strictly selected in order to guarantee the intended gastroresistance.

The gastroresistant film coats each granule completely and makes the dosage form insoluble in acid media, but quickly disintegrable for neutral and alkaline pH values, as in the case of the fluids present in the proximal fraction of the small intestine, where the dissolution and the absorption of the benzimidazole(s) will occur. The thickness of this layer should be not be less than 30 μm, in order to guarantee effective protection.

The final product is sieved in rooms with controlled humidity and temperature, and placed in hard gelatine capsules.

The dosage forms of the present invention are multi-unitary formulations in the form of pellets characterized by:
a) a spherical inert core coated with several concentric layers which results in a product of spherical symmetry, b) a first layer of a thickness of 150–250 μm, applied to the inert core, containing at least one benzimidazole or a pharmaceutically acceptable salt thereof, mixed with inert substances that are also pharmaceutically acceptable, c) a second layer (intermediate layer), of a strictly polymeric nature and a minimum thickness of 15 μm, and d) a third layer (the outside layer), constituted by a gastroresistant or enteric polymer, of a minimum thickness of 30 μm. Moreover, the formulations are characterized by the complete absence of residues of organic solvents and the impurities associated to them, a characteristic which, among others, distinguishes them from the other formulations on the market.

The dosage forms produced by extrusion/spheronization methods are completely outside the scope of the present invention, because the pellets produced have preponderantly axial symmetry, whereas the dosage forms of the present invention have spherical symmetry, as well as other differences of a structural nature (number of layers, presence of an inert core from which the growth of the pellet begins during its preparation, etc.).

Below, there are some examples of formulations that were obtained during the optimization process until the final formulations were produced.

EXAMPLES

TABLE I

Qualitative and quantitative composition of dosage forms containing omeprazole (90 ± 10 mg of omeprazole/g of pellets) according to the invention.

| | Example 1 (g) | Example 2 (g) | Example 3 (g) | Example 4 (g) | Example 5 (g) | Example 6 (g) | Example 7 (g) | Example 8 (g) | Example 9 (g) | Example 10 (g) |
|---|---|---|---|---|---|---|---|---|---|---|
| COMPOSITION | | | | | | | | | | |
| Inert cores | 1000.0 | 1000.0 | 1000.0 | 1000.0 | 1000.0 | 1000.0 | 1000.0 | 1000.0 | 1000.0 | 1000.0 |
| Active layer: | | | | | | | | | | |
| Omeprazole | 140 | 140 | 140.0 | 140.0 | 140.0 | 140.0 | 140.0 | 140.0 | 140.0 | 140.0 |
| Sodium dodecyl sulfate | 2.7 | 2.7 | 4.0 | 4.0 | 4.0 | 4.0 | 4.0 | — | — | — |
| Sodium starch glycolate | 4.3 | 4.3 | 4.3 | 4.3 | 4.3 | 4.3 | 4.3 | 4.0 | 4.0 | 4.0 |
| Hydroxypropy methyl-cellulose | 11.0 | 11.0 | 11.0 | 11.0 | 11.0 | 11.0 | 11.0 | 56.3 | 56.3 | 56.3 |
| Sodium Tetraborate | 29.5 | 29.5 | 29.5 | 29.5 | 29.5 | 29.5 | 29.5 | 1.8 | 1.8 | 1.8 |
| Lactose | 63.2 | 47.2 | 45.3 | 45.3 | 45.3 | 45.3 | 45.3 | — | — | — |
| Emulsion 30% Si-methicone | 0.9 | 0.9 | 0.9 | 0.9 | 0.9 | 0.9 | 0.9 | 0.9 | 0.9 | 0.9 |
| Glycerol polyethylene glycoloxystearate | — | — | — | — | — | — | — | 8.3 | 8.3 | 8.3 |
| Talc | — | — | — | — | — | — | — | — | 2.5 | — |
| Insulating layer: | | | | | | | | | | |
| Hydroxypropy methyl-cellulose | 40 | 40.0 | 40.0 | 40.0 | 46.7 | 80.0 | 80.0 | 80.0 | 80.0 | 80.0 |
| Enteric layer: | | | | | | | | | | |
| Copolymer of methacrylic acid | 150 | 225.0 | 250.0 | 258.7 | 555.0 | 225.0 | 150.0 | 225.0 | 225.0 | 225.0 |
| Triethlcitrate | 15.0 | 22.5 | 25.0 | 25.9 | 55.0 | 22.5 | 15.0 | 22.5 | 22.5 | 22.5 |
| Emulsion 30% Si-methicone | 0.9 | 1.5 | 1.7 | 1.8 | 3.8 | 1.5 | 1.0 | 1.5 | 1.5 | 1.5 |
| TOTAL | 1457.5 | 1524.6 | 1551.7 | 1561.4 | 1895.5 | 1564.0 | 1481.0 | 1540.0 | 1542.8 | 1540.3 |
| Assay mg/g (theoretical value) | 96.1 | 91.8 | 90.2 | 89.7 | 73.9 | 89.5 | 94.5 | 90.9 | 90.7 | 90.9 |
| Tests | | | | | | | | | | |
| Assay (mg/g) | 79.6 | 80.0 | 78.5 | 77.8 | 67.8 | 81.2 | 85.6 | 89.3 | 85.5 | 87.4 |
| (%) | (82.8%) | (87.1%) | (87.0%) | (86.7%) | (91.8%) | (90.7%) | (90.6%) | (98.2%) | (94.5%) | (96.1%) |
| Gastroresistance (%) | 14.9 | 19.4 | 39.5 | 62.8 | 95.0 | 96.2 | 91.3 | 98.0 | 96.7 | 96.5 |
| Dissolution (%) | — | — | — | — | 84.3 | 93.3 | 86.3 | 91.8 | 96.5 | 96.3 |

The formulations presented in Examples 1–10 were obtained from inert cores coated successively by the three layers, each one with the composition presented in Table I.

The pharmaceutical formulations of the present invention take the form of pellets with which hard gelatine capsules are filled. The preparation of the pellets is processed as follows. For the preparation of the layer containing the active substance(s) (1st layer or active layer), a portion of demineralized water was heated up to 85–90° C. and then hydroxypropylmethylcellulose (HPMC) was dispersed in it. In another portion of demineralized water, glycerol polypropyleneglycol oxystearate, sodium tetraborate, the simethicone emulsion, sodium starch glycolate and, finally, benzimidazole(s) were dispersed. When the suspension became uniform it was mixed with the HPMC dispersion after cooling to about 35° C. This last suspension was homogenized by shaking and applied to the inert cores (710–850 μm or 850–1000 μm). After the application of the suspension, the pellets were dried so that their temperature did not exceed 50° C.

For the preparation of the insulating layer (2nd layer or intermediate layer), demineralized water was heated up to 85–90° C. After this temperature was reached, HPMC was added and homogenized by shaking, until total dispersion was achieved. The dispersion was cooled to room temperature and applied to the product already containing the benzimidazolic layer. This operation is extremely delicate, because it must be guaranteed that the fluidization of the bed ensures the homogenous coating of all the pellets, with a film of regular thickness (which should not be less than 15 μm).

The gastroresistant or enteric coating layer (3rd layer or external layer) was prepared by mixing the demineralized water with the simethicone emulsion, followed by the addition of triethylcitrate and, finally, the copolymer of methacrylic acid. The dispersion was then homogenized for a few minutes and applied to the pellets already coated with the intermediate layer.

All the stages of the manufacture of the dosage forms took place in a fluid bed equipment with an inner partition device (wurster), under specific conditions.

As regards the final products, the amount of the active ingredient (mg of omeprazole/g of pellets), as well as the gastroresistance (%) and dissolution parameters of the formulations, were determined. The objective established for this invention was the obtention of dosage forms with the following characteristics: amount of active ingredient$\geq$85 mg/g of pellets, gastroresistance$\geq$95% and dissolution$\geq$85%, in order to establish the following specification limits (which should be maintained throughout the period of validity of the product): amount of active ingredient$\geq$80.75 mg/g of pellets, gastroresistance$\geq$85%, dissolution$\geq$75%.

The analysis of the results obtained in the assays performed with the different dosage forms in the Examples presented in Table I led to the following conclusions:

a) The dosage form illustrated in Example 1 did not present enough gastroresistance.
b) The dosage form illustrated in Example 2 is similar to that of Example I, but the amount of enteric polymer was increased (3rd layer). This change was not enough to significantly improve the gastroresistence of the dosage form.
c) Examples 3 and 4 illustrate dosage forms wherein, preponderantly, the amount of gastroresistant polymer was increased, but their gastroresistance do not reached the intended levels.
d) Example 5 illustrates a formulation wherein the amount of enteric polymer was duplicated. At the same time, the thickness of the intermediate layer was increased slightly. Using this strategy it was possible to obtain pellets with the intended gastroresistance. However, the thickness of the gastroresistant layer seems to have a negative influence on the dissolution of the formulation.
e) Example 6 illustrates a formulation wherein the amount of hydroxypropylmethylcellulose used in the 2nd layer was doubled and the amount of gastroresistant polymer used was the same as in Example 2. Under these conditions, a gastroresistance value of 96.2% and a dissolution value of 93.3% were obtained.
f) Example 7 illustrates a dosage form wherein it was investigated whether maintaining the thickness of the 2nd layer made it possible to further reduce the amount of gastroresistant polymer to be applied. The results obtained in the gastroresistance and dissolution assays show that it is not advisable to reduce the amount of gastroresistant polymer beyond the values used in Examples 2 and 6.
g) Examples 8, 9 and 10 illustrate dosage forms wherein an attempt was made to improve the yield of application of the 1st layer, without affecting the dissolution of the dosage form. In Example 8, sodium dodecyl sulphate was substituted by glycerol polyethyleneglycol oxystearate, the use of lactose was excluded and the percentage of hydroxypropylmethylcellulose (HPMC) was increased considerably. In Example 9, the amount of sodium tetraborate was corrected to adjust the pH value to about 9 and some talc was also included. Example 10 is similar to Example 9, except that talc was not included as a lubricant.
h) The results obtained with the dosage forms illustrated in Examples 8, 9 and 10 suggest that the changes made to the composition of the 1st layer made it possible to increase by about 5% the yield of the industrial process for the application of the first layer, without affecting the dissolution of the dosage form.

The Examples presented above showed that is possible, using only aqueous solvents, to obtain formulations containing omeprazole which obey the dissolution and gastroresistance criteria required for these types of dosage forms. Examples 1–4 describe dosage forms which are executable from a technological point of view, but which do not obey the other criteria required for the type of dosage form intended to be developed. Examples 5–10 describe dosage forms that obey the established criteria (i.e. GR$\geq$85% and dissolution$\geq$75%). However, the dosage forms illustrated in Examples 5–7 are economically not very advantageous, because the yield for application of the 1st layer, the one that contains omeprazole, was still relatively low (i.e. about 90%), taking into account the high price of this active ingredient. Examples 8–10 constitute steps for optimizing the dosage forms in order to improve the yield of the industrial process, as a way of making it economically more advantageous.

The present invention also relates to the preparation of other omeprazole multi-unitary dosage forms, of greater potency (i.e. 140±10 mg of omeprazole/g of pellets), for treatment with higher dosages (i.e. 40 mg/capsule), also using hard gelatine capsules of small dimensions for increased patient comfort. In order to achieve this, inert cores of smaller dimensions are used (600–710 μm). Two Examples of these formulations are presented as follows:

TABLE II

Qualitative and quantitative composition of dosage forms containing omeprazole (140 ± 10 mg of omeprazole/g of pellets) according to the invention.

| COMPOSITION | Example 11 | Example 12 |
|---|---|---|
| | (g) | (g) |
| Inert cores | 1000.0 | 1000.0 |
| Active layer | | |
| Omeprazole | 280.0 | 280.0 |
| Sodium starch glycolate | 8.0 | 8.0 |
| Hydroxypropylmethylcellulose | 112.6 | 112.6 |
| Sodium tetraborate | 3.0 | 3.0 |
| Emulsion 30% Simethicone | 1.8 | 1.8 |
| Glycerol polyethyleneglycol oxystearate | 16.3 | 16.3 |

TABLE II-continued

Qualitative and quantitative composition of dosage forms containing omeprazole (140 ± 10 mg of omeprazole/g of pellets) according to the invention.

| COMPOSITION | Example 11 | Example 12 |
|---|---|---|
| Talc | — | 5.0 |
| Insulating layer | | |
| Hydroxypropylmethylcellulose | 140.0 | 140.0 |
| Enteric layer | | |
| Copolymer of methacrylic acid | 390.0 | 390.0 |
| Triethylcitrate | 39.0 | 39.0 |
| Emulsion 30% Simethicone | 2.6 | 2.6 |
| TOTAL | 1993.3 | 1998.3 |
| Assay mg/g (theoretical value) | 140.5 | 140.1 |
| Tests | | |
| Assay (mg/g) (%) | 133.6 | 134.8 |
| | (95.1%) | (96.2%) |
| Gastroresistance (%) | 96.1 | 95.0 |
| Dissolution (%) | 89.7 | 85.4 |

The preparation of the suspensions and dispersions for the manufacture of the product was carried out in the same manner as described previously.

In the case of these higher potency omeprazole dosage forms, since the inert cores have smaller dimensions, it was necessary to adjust the amount of hydroxypropylmethylcellulose to be incorporated into the intermediate layer in order to guarantee adequate insulation (i.e. thickness greater than 15 $\mu$m). It is also necessary to study the amount of enteric polymer coating to include in the formulation in order to obtain a layer with a thickness greater than 30 $\mu$m.

Just as it was possible to establish stable dosage forms for omeprazole (as shown later on), the present invention also seeks to describe multi-unitary dosage forms containing lansoprazole. Some Examples are presented below.

The preparation of the suspensions and dispersions was carried out according to the methodology described previously.

All the formulations illustrated in the Examples present assay, gastroresistance and dissolution parameters compatible with the requirements. Products manufactured in accordance with these Examples were submitted to long-term stability assays, the results of which are presented below.

TABLE III

Qualitative and quantitative composition of dosage forms containing lansoprazole (90 ± 10 mg of lansoprazole/g of pellets) according to the invention.

| COMPOSITION | Example 13 | Example 14 | Example 15 |
|---|---|---|---|
| | (g) | (g) | (g) |
| Inert cores | 1000.0 | 1000.0 | 1000.0 |
| Active layer | | | |
| Lansoprazole | 140 | 140 | 140.0 |
| Glycerol polyethyleneglycol oxystearate | 8.3 | 8.3 | 8.3 |
| Sodium starch glycolate | 4.0 | 4.0 | 4.0 |
| Hydroxypropylmethylcellulose | 56.3 | 56.3 | 56.3 |
| Sodium tetraborate | 1.5 | 1.5 | 1.8 |
| Emulsion 30% Simethicone | 0.9 | 1.3 | 2.0 |

TABLE III-continued

Qualitative and quantitative composition of dosage forms containing lansoprazole (90 ± 10 mg of lansoprazole/g of pellets) according to the invention.

| COMPOSITION | Example 13 | Example 14 | Example 15 |
|---|---|---|---|
| Talc | — | — | — |
| Insulating layer | | | |
| Hydroxypropylmethylcellulose | 80.0 | 80.0 | 80.0 |
| Gastroresistant layer | | | |
| Copolymer of methacrylic acid | 225.0 | 225.0 | 225.0 |
| Triethylcitrate | 22.5 | 22.5 | 22.5 |
| Emulsion 30% Simethicone | 1.5 | 1.5 | 1.5 |
| TOTAL | 1540.0 | 1540.4 | 1541.4 |
| Assay mg/g (theoretical value) | 90.9 | 90.9 | 90.8 |
| Tests | | | |
| Assay (mg/g) (%) | 90.5 | 89.0 | 88.6 |
| | (99.6%) | (97.9%) | (97.6%) |
| Gastroresistance (%) | 92.3 | 94.0 | 95.1 |
| Dissolution (%) | 84.8 | 85.0 | 82.7 |

The present invention also applies to the active ingredient pantoprazole, with which multi-unitary dosage forms were also developed similar to the ones obtained for the other substituted benzimidazoles (omeprazole and lansoprazole). One Example of this application is presented below.

TABLE IV

Qualitative and quantitative composition of dosage forms containing pantoprazole (90 ± 10 mg of pantoprazole/g of pellets) according to the invention.

| COMPOSITION | Example 16 (0) |
|---|---|
| | (g) |
| Inert cores | 1000.0 |
| Active layer | |
| Pantoprazole | 140 |
| Glycerol polyethylenoglycol oxystearate | 8.3 |
| Sodium starch glycolate | 4.0 |
| Hydroxypropyl methylcellulose | 56.3 |
| Sodium tetraborate | 2.0 |
| Emulsion 30% Simethicone | 1.8 |
| Insulating layer | |
| Hydroxypropylmethylcellulose | 80.0 |
| Gastroresistant layer | |
| Copolymer of methacrylic | 225.0 |
| Triethylcitrate | 22.5 |
| Emulsion 30% Simethicone | 1.5 |
| TOTAL | 1541.4 |
| Assay mg/g (theoretical value) | 90.8 |
| Tests | |
| Assay (mg/g) (%) | 90.0 |
| | (99.1%) |
| Gastroresistance (%) | 93.8 |
| Dissolution (%) | 87.6 |

The present invention can extends its application to other substituted benzimidazoles with therapeutic interest, for example leminoprazole and/or pariprazole. It is also applicable to substituted benzimidazole salts, benzimidazolic associations or pharmaceutically acceptable salts thereof.

With optimized dosage forms—final dosage forms—it will be shown below that the products obtained, as well as obeying analytic specifications when analyzed immediately after manufacture, maintain their stability during a period of time appropriate for sale on the pharmaceutical market for therapeutic purposes.

Control of the Finished Product

Parameters analyzed:
Assay
Gastroresistance
Dissolution
Total impurities.

The above mentioned parameters were determined by HPLC (High Performance Liquid Chromatography), with an RP-8 column of 150 mm×46 mm, filled with particles of 5 μm, and spectrophotometric detection at λ=280 nm. In order to determine the total impurities, an RP-8 column of 250 mm×46 mm was used.

The gastroresistance assays were performed by submitting the dosage forms, for 2 hours, to the action of an acidic incubation medium of pH≈1.2, at 37° C.±0.5° C., with constant mixing at 100 r.p.m.±4 r.p.m., using the dissolution equipment described by USP.

The dissolution assays were performed by submitting the dosage forms, for 2 hours, to the action of an acidic incubation medium of pH≈1.2, at 37° C.±5° C., with constant mixing at 100 r.p.m.±4 r.p.m., followed by the addition a dissolution incubation medium, maintaining the same conditions for 30 min, using the dissolution equipment described by USP.

Stability Tests

To test the stability of the pharmaceutical dosage forms, stability tests were performed on batches of capsules containing the pellets manufactured according to the present invention. The pellets were placed inside hard gelatine capsules which were stored in blisters of polyamide/aluminium/PVC sealed with aluminium foil of 25 μm. These blisters are maintained at room temperature (real time) and also in an incubator at 40° C. and 75% relative humidity, and certain parameters were periodically determined, such as assay, gastroresistance, dissolution total impurities. The results obtained for one batch of omeprazole pellets or one batch of lansoprazole pellets are presented as follows.

TABLE V

BATCH MED59-OMEPRAZOLE PELLETS
Assays performed with product maintained at 4° C./75% relative humidity

| Incubation period (months) | Temperat. (° C.) | Relative Humidity (%) | Colour | Assay (mg/g) (%) | Gastro-resistance (%) | Dissolution (%) | Impurities Total Individual (%) |
|---|---|---|---|---|---|---|---|
| 0 | 40 | 75 | A | 88.9 (100.0) | 96.3 | 93.6 | <2.0 <0.5 |
| 1 | 40 | 75 | A | 86.7 (97.5) | 98.8 | 87.6 | <2.0 <0.5 |
| 3 | 40 | 75 | A | 88.9 (100.0) | 97.6 | 87.2 | <2.0 <0.5 |
| 5 | 40 | 75 | A | 86.6 (97.4) | 94.5 | 82.1 | <2.0 <0.5 |
| 6 | 40 | 75 | A | 85.8 (96.5) | 97.5 | 86.7 | <2.0 <0.5 |
| 7 | 40 | 75 | A | 86.0 (96.5) | 92.1 | 83.0 | <2.0 <0.5 |
| 9 | 40 | 75 | A | 84.0 (94.5) | 93.5 | 84.8 | <2.0 <0.5 |

A-White Pearl
The World Health Organisation considers that accelerated stability studies using incubation conditions of a temperature of 40° C. and 75% relative humidity for 3 months in temperate and subtropical climates and 6 months in hot climates for products that are intended for the global market are a good indicator of the stability of a pharmaceutical dosage form. (WHO/PHARM/94.565).

TABLE VI

BATCH MED59-OMEPRAZOLE PELLETS
Assays performed with product maintained at room temperature (real time)

| Incubation period (months) | Temperat. (° C.) | Relative Humidity (%) | Colour | Assay (mg/g) (%) | Gastro-resistance (%) | Dissolution (%) | Impurities Total Individual (%) |
|---|---|---|---|---|---|---|---|
| 0 | 25 | 60 | A | 88.9 (100.0) | 96.3 | 93.6 | <2.0 <0.5 |
| 6 | 25 | 60 | A | — | — | — | — |
| 9 | 25 | 60 | A | 89.0 (100.0) | 96.3 | 86.0 | <2.0 <0.5 |
| 12 | 25 | 60 | A | 88.0 (99.0) | 96.1 | 84.4 | <2.0 <0.5 |

TABLE VI-continued

BATCH MED59-OMEPRAZOLE PELLETS
Assays performed with product maintained at room temperature (real time)

| Incubation period (months) | Temperat. (° C.) | Relative Humidity (%) | Colour | Assay (mg/g) (%) | Gastro- resistance (%) | Dissolution (%) | Impurities Total Individual (%) |
|---|---|---|---|---|---|---|---|
| 18 | 25 | 60 | A | 89.4 (100.6) | 95.1 | 86.5 | <2.0 <0.5 |

A-White Pearl

TABLE VII

BATCH LAN1-LANSOPRAZOLE PELLETS
Assays performed with product maintained at 40° C./75% relative humidity

| Incubation period (months) | Temperat. (° C.) | Relative Humidity (%) | Colour | Assay (mg/g) (%) | Gastro- resistance (%) | Dissolution (%) | Impurities Total Individual (%) |
|---|---|---|---|---|---|---|---|
| 0 | 40 | 75 | A | 90.5 (100.0) | 90.9 | 83.1 | <2.0 <0.5 |
| 1 | 40 | 75 | A | 90.5 (100.0) | 92.1 | 82.9 | <2.0 <0.5 |
| 3 | 40 | 75 | A | 86.3 (95.4) | 92.9 | 81.2 | <2.0 <0.5 |
| 6 | 40 | 75 | A | 87.1 (96.2) | 91.2 | 80.7 | <2.0 <0.5 |

A-White Pearl
The World Health Organisation considers that accelerated stability studies using incubation conditions of a temperature of 40° C. and 75% relative humidity for 3 months in temperate and subtropical climates and 6 months in hot climates for products that are intended for the global market are a good indicator of the stability of a pharmaceutical dosage form. (WHO/PHARM/94.565).

TABLE VIII

BATCH LAN1-LANSOPRAZOLE PELLETS
Assays performed with product maintained at room temperature (real time)

| Incubation period (months) | Temperat. (° C.) | Relative Humidity (%) | Colour | Assay (mg/g) (%) | Gastro- resistance (%) | Dissolution (%) | Impurities Total Individual (%) |
|---|---|---|---|---|---|---|---|
| 0 | 25 | 60 | A | 90.5 (100.0%) | 90.9 | 83.1 | <2.0 <0.5 |
| 6 | 25 | 60 | A | 90.5 (100.0%) | 89.1 | 82.0 | <2.0 <0.5 |
| 9 | 25 | 60 | A | — | — | — | — |
| 12 | 25 | 60 | A | 90.3 99.8% | 92.3 | 84.8 | <2.0 <0.5 |

DISCUSSION

The Examples presented above show that the dosage forms of the present invention present good stability during a long period of storage (i.e. at least 3 years) and present gastroresistance parameters suitable for the length of time that the product stays in the stomach, being quickly dissolved as soon as it reaches the proximal portion of the small intestine. For these reasons, the formulations should present the following characteristics:

1) An inert core of spherical symmetry constituted by pharmaceutically acceptable inert excipients, which serves as the support on which the remaining elements of the formulation are deposited.
2) A layer containing at least one benzimidazole (i.e. omeprazole, lansoprazole or pantoprazole or other substituted benzimidazoles of therapeutic interest), or their various pharmaceutically acceptable salts, mixed in an appropriate proportion with pharmaceutically acceptable inert excipients, whose properties guarantee the disaggregation of the formulation and the dissolution of the active ingredient in the chosen site.
3) An insulating layer of a strictly polymeric nature, water-soluble, free from alkaline or alkaline-earthy metallic salts, of a minimum thickness of 15 $\mu$m, which separates the active layer from the gastroresistant or enteric layer.
4) An enteric coating layer, generally constituted by an acrylic polymer, of a minimum thickness of 30 $\mu$m, possibly in the presence of a plasticizer and/or an antifoaming agent, insoluble at the gastric pH and easily disaggregable at the pH of the proximal part of the small intestine.
5) Total absence of residues of organic solvents or the impurities associated to them, since the formulation is produced exclusively using demineralized water.

The results obtained show that the dosage forms of the present invention are stable in terms of dosage as well as in terms of the other tested parameters (i.e. gastroresistance, dissolution and impurities). The process used to manufacture the products is economically more advantageous than the other inventions which belong to the current state of the art, and it also presents novelty as regards its applications. The technological process used is incomparably safer than the ones already described, since it does not require the use of organic solvents, with a toxicity risk to operators or an explosion risk. Moreover, the pharmaceutical dosage form itself is safer, since there are no residues of organic solvents or the impurities inherent to them in the finished products, which is an advantage of these products in relation to the others in terms of public health.

In addition, the whole manufacturing process takes place in the same equipment—a fluid bed equipment with an inner partition device (wurster), which produces pellets of high sphericity and a flat surface, constituted by various layers of uniform thickness, contrary to what happens with the pellets produced by extrusion/spheronization, by rotogranulation or in conventional coating pans.

The pharmacist can always make variations to the pellet formulations of the present invention, for example the use of other aqueous polymers to ensure gastroresistance, such as aqueous dispersions of cellulose acetophtalate (CAP), or other plasticizers such as tributylcitrate (Citroflex®-4), acetyltributylcitrate (Citroflex®-A4), dibutyl sebacate (DBS), diethylphtalate (DEP), monoglyceride acetylated (Myvacet® 9-40), of other aggregants such as methylcellulose, ethylcellulose, hydroxyethylcellulose, hydroxypropylcellulose, polyethylene glycol, polyvinylpyrrollidone, etc., of other disaggregants such as pregelatinized starch, microcrystalline cellulose, calcic or sodic carboxymethylcellulose or sodium alginate, or other surfactant agents such as sodium trilaurylsulfate, sodium tridecylethoxylate, sodium myristilsulfate or sorbitane esters, without going beyond the spirit and scope of the present invention. The invention can also be applied to benzimidazolic associations or pharmaceutically acceptable salts thereof, if this can be justified in therapeutic terms.

Finally, it should be pointed out that the present invention does not include formulations obtained by the classic extrusion/spheronization techniques already known from the state of the art, the products of which, in terms of qualitative and quantitative composition and also structurally, are different from the ones that the present invention intends to protect.

What is claimed is:

1. Stable pellet pharmaceutical preparations containing substituted benzimidazole(s) or their salts, characterized in that they contain a quantity of active ingredient of between 1 and 50 mg, an inert core of spherical symmetry with a diameter of 600–1000$\mu$, constituted by inert excipients, coated with an active layer containing at least one substituted benzimidazole or its salt in the micronized form, sodium tetraborate to improve the stability of the benzimidazole or its salt and various pharmaceutically acceptable inert excipients, mixed in suitable proportions in order to allow the disaggregation of the formulations and dissolution of the active ingredient(s), coated in turn with an insulating layer consisting of a water soluble polymer and any residual water, and being free from alkaline and/or alkaline-earthy metallic salts, of a minimum thickness of 15 $\mu$m, this layer being coated lastly with a gastroresistant or enteric layer of a minimum thickness of 30 $\mu$m.

2. Pharmaceutical preparations according to claim 1, characterized in that the layer which contains the substituted benzimidazole or its salt comprises less than 2% (in weight) of a disaggregating agent selected from the group consisting of sodium starch glycolate, pregelatinized starch, microcrystalline cellulose, sodic or calcic carboxymethylcellulose, sodium alginate and mixtures thereof.

3. Pharmaceutical preparations according to claim 1, characterized in that the active layer containing the substituted benzimidazole or its salts comprises less than 5% (in weight) of a surfactant.

4. Pharmaceutical preparations according to claim 1, characterized by an insulating layer which is soluble and/or easily disaggregable in water, free from alkaline and/or alkaline-earthy metallic salts, and wherein the water soluble polymer is a binding agent(s) present in a percentage of 5–10% in weight (in relation to the final weight of the product).

5. Pharmaceutical preparations according to claim 1, characterized in that the gastroresistant or enteric layer only contains aqueous polymers consisting essentially of anionic copolymers of methacrylic acid and ethyl acrylate or cellulose acetophtalate, present in a percentage of 14–20% (in weight), in relation to the final weight of the preparation, mixed with one or more pharmaceutically acceptable plasticizers.

6. Pharmaceutical preparations according to any one of claims 1–5, characterized in that they are free from organic solvents or residues inherent to them and contain less than 1.5% humidity (in weight).

7. Pharmaceutical preparations according to claim 6 such that the preparations display and maintain the characteristics relating to the amount of the active ingredient, gastroresistance, dissolution and total impurities suitable for a period of validity of 3 years.

8. Pharmaceutical preparations according to claim 3 wherein the surfactant is selected from the group consisting of sodium dodecylsulfate, sodium trilaurylsulfate, sodium tridecyletoxylate, sodium miristylsulfate, fatty acids of sorbitan esters and mixtures thereof.

9. Pharmaceutical preparations according to claim 8 wherein the surfactant is glycerol polyethylene glycol oxystearate.

10. Pharmaceutical preparations according to claim 4, characterized in that the binder agent(s) is selected from the group consisting of methyl cellulose, ethyl cellulose, hydroxymethylcellulose, hydroxypropylcellulose, hydroxypropyl methyl cellulose, polyvinyl pirrollydone, polyethylene glycols and mixtures thereof.

11. Pharmaceutical preparations according to claim 5, characterized in that the plasticizers are selected from the group consisting of triethylcitrate, tributylcitrate, acetyltributylcitrate, dibutylsebacate, diethylphtalate, monoglyceride acetylated, and polyethylenoglycols, present in a percentage of 1.0% and 2.%, mixed with an antifoaming agent, present in a percentage lower than 0.5% and possibly a lubricant.

12. Pharmaceutical preparations according to claim 11 wherein the antifoaming agent is a silicon material.

13. Pharmaceutical preparations according to claim 11 wherein the lubricant is talc or colloidal silicon dioxide.

* * * * *